United States Patent
Pursley

(10) Patent No.: US 9,867,530 B2
(45) Date of Patent: Jan. 16, 2018

(54) TELESCOPIC SIDE PORT CATHETER DEVICE WITH IMAGING SYSTEM AND METHOD FOR ACCESSING SIDE BRANCH OCCLUSIONS

(71) Applicant: Volcano Corporation, San Diego, CA (US)

(72) Inventor: Matt D. Pursley, Alpharetta, GA (US)

(73) Assignee: VOLCANO CORPORATION, San Diego, CA (US)

( * ) Notice: Subject to any disclaimer, the term of this patent is extended or adjusted under 35 U.S.C. 154(b) by 452 days.

(21) Appl. No.: 13/841,476

(22) Filed: Mar. 15, 2013

(65) Prior Publication Data

US 2013/0303897 A1 Nov. 14, 2013

Related U.S. Application Data

(63) Continuation-in-part of application No. 11/838,297, filed on Aug. 14, 2007, now Pat. No. 9,233,224.
(Continued)

(51) Int. Cl.
*A61B 1/313* (2006.01)
*A61B 1/00* (2006.01)
(Continued)

(52) U.S. Cl.
CPC .......... *A61B 1/3137* (2013.01); *A61B 1/0051* (2013.01); *A61B 1/01* (2013.01);
(Continued)

(58) Field of Classification Search
CPC .................................................. A61B 1/3137
See application file for complete search history.

(56) References Cited

U.S. PATENT DOCUMENTS 3,301,258 A 1/1967 Werner
3,617,880 A 11/1971 Cormack et al.
(Continued)

FOREIGN PATENT DOCUMENTS

EP 1041373 A2 10/2000
EP 01172637 A1 1/2002
(Continued)

OTHER PUBLICATIONS

Abdi et al., 2010, Principal component analysis, Wiley Interdisciplinary Reviews: Computational Statistics 2:433-459.
(Continued)

*Primary Examiner* — Serkan Akar

(57) ABSTRACT

A medical device and method are provided for accessing a side branch in an artery utilizing an on-board imaging device. The device includes a catheter having a sidewall, an internal lumen, and a side port formed through the sidewall. A perforating guide wire has a proximal portion within the internal lumen and a distal portion arranged to be movable out of the side port. The guide wire can be delivered through the side port to a side branch artery when the catheter is deployed to a location with the side port aligned with the side branch artery. In one embodiment, the catheter includes an on-board imaging system disposed adjacent the side opening. The imaging system images tissue adjacent the side opening to assist with alignment of the guide wire to enter a side branch and/or cross an occlusion within the side branch.

15 Claims, 14 Drawing Sheets

Related U.S. Application Data

(60) Provisional application No. 60/837,900, filed on Aug. 14, 2006.

(51) Int. Cl.
*A61B 8/00* (2006.01)
*A61B 5/00* (2006.01)
*A61B 1/04* (2006.01)
*A61B 8/12* (2006.01)
*A61B 1/005* (2006.01)
*A61B 1/01* (2006.01)
*A61B 1/018* (2006.01)
*A61M 25/01* (2006.01)
*A61M 25/00* (2006.01)
*A61M 25/09* (2006.01)
*A61B 17/22* (2006.01)

(52) U.S. Cl.
CPC ............... *A61B 1/018* (2013.01); *A61B 1/04* (2013.01); *A61B 5/0066* (2013.01); *A61B 5/0084* (2013.01); *A61B 8/12* (2013.01); *A61B 8/445* (2013.01); *A61M 25/0082* (2013.01); *A61M 25/01* (2013.01); *A61B 1/00082* (2013.01); *A61B 8/4488* (2013.01); *A61B 2017/22095* (2013.01); *A61M 25/09* (2013.01); *A61M 2025/0096* (2013.01); *A61M 2025/0175* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |

(56) References Cited

U.S. PATENT DOCUMENTS

| | | |
|---|---|---|
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |

(56) References Cited

U.S. PATENT DOCUMENTS

| | | |
|---|---|---|
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |

(56) References Cited

U.S. PATENT DOCUMENTS

| | | |
|---|---|---|
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0047165 A1* | 11/2001 | Makower ............ A61B 8/12 604/528 |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |

(56) References Cited

U.S. PATENT DOCUMENTS

| | | |
|---|---|---|
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2005/0267458 A1* | 12/2005 | Paul .............. A61B 18/1492 606/41 |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |

(56) References Cited

U.S. PATENT DOCUMENTS

| | | |
|---|---|---|
| 2007/0201736 A1 | 8/2007 | Klingensmith et al. |
| 2007/0206193 A1 | 9/2007 | Pesach |
| 2007/0208256 A1* | 9/2007 | Marilla .................. 600/467 |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1* | 10/2009 | Courtney ............. A61B 5/0062 600/463 |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |

(56) References Cited

U.S. PATENT DOCUMENTS

| | | |
|---|---|---|
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A1 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |

(56) References Cited

FOREIGN PATENT DOCUMENTS

| WO | 2006/111704 A1 | 10/2006 |
|---|---|---|
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/006886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15(3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.

(56) References Cited

OTHER PUBLICATIONS

Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).

(56) References Cited

OTHER PUBLICATIONS

Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846, original document published in 2000.
Machine translation of JP 2000-321034, original document published in 2000.
Machine translation of JP 2000-329534, original document published in 2000.
Machine translation of JP 2004-004080, original document published in 2004.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results. Eur. Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, publsihed on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.

(56) References Cited

OTHER PUBLICATIONS

Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.

\* cited by examiner

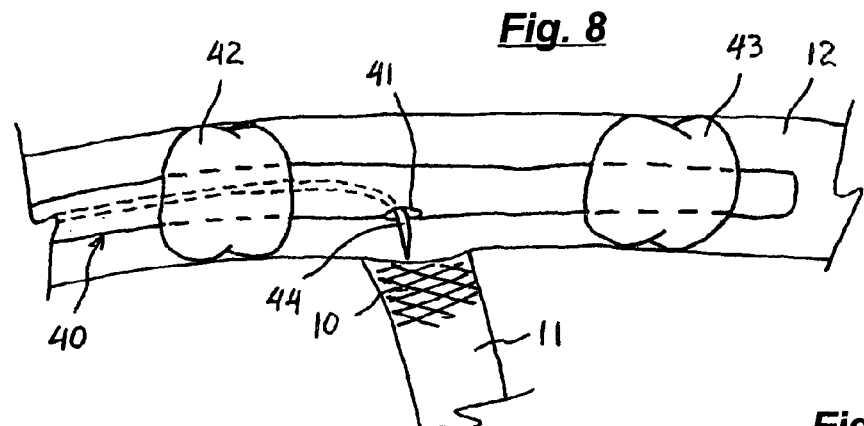
Fig. 8
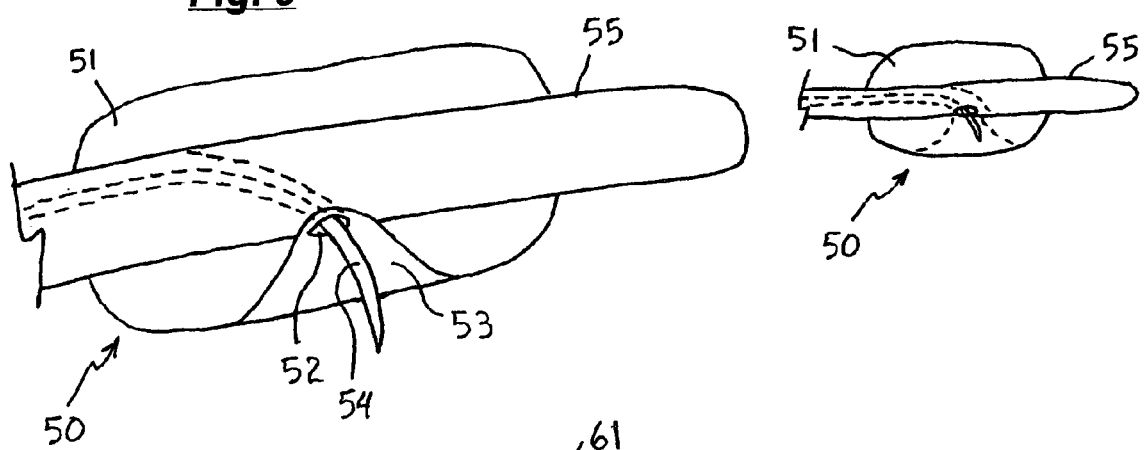
Fig. 9
Fig. 10
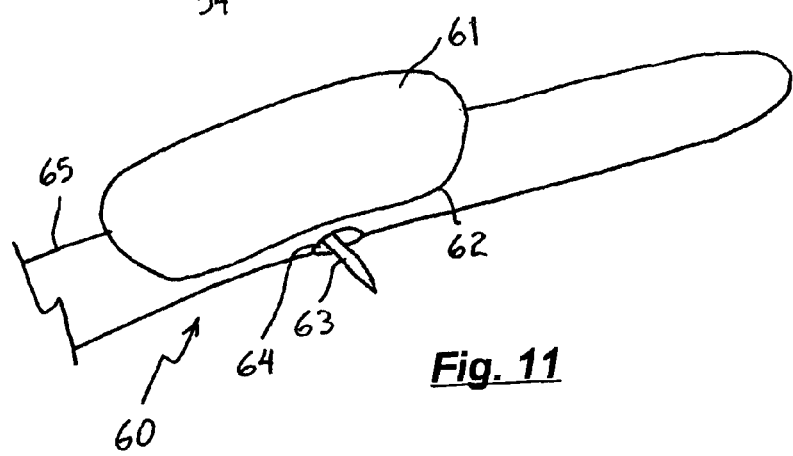
Fig. 11

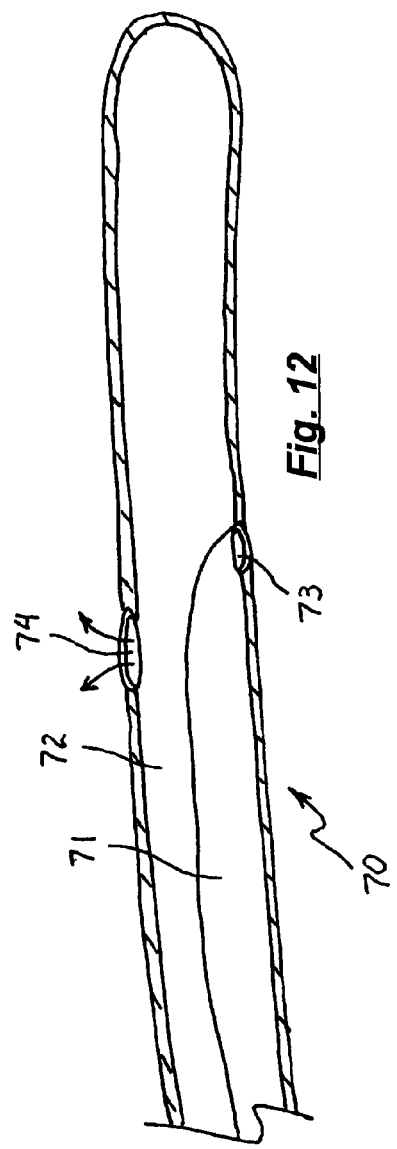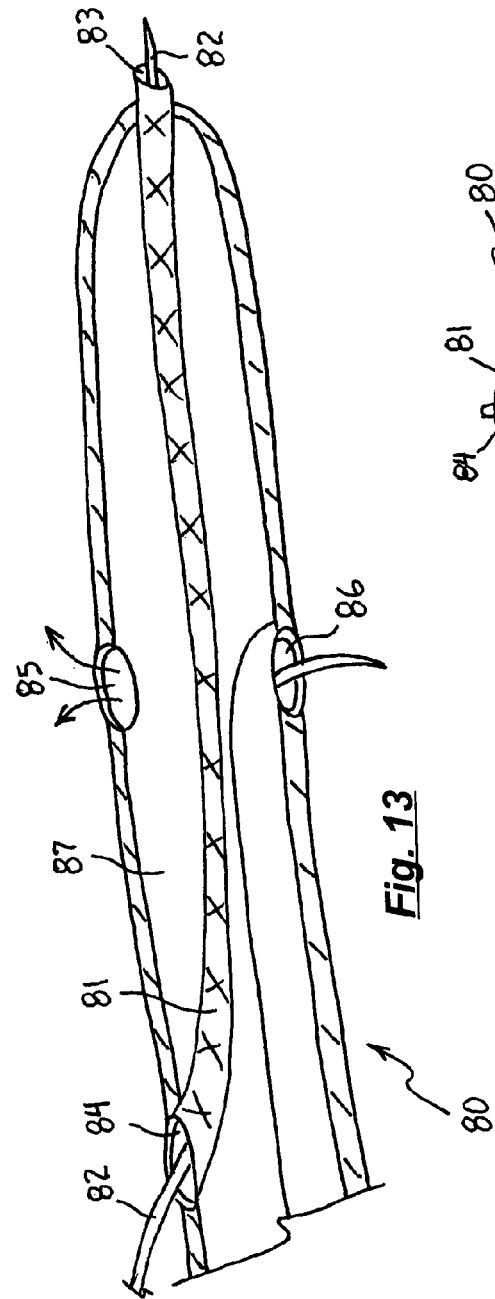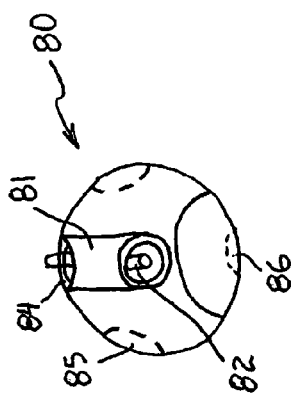

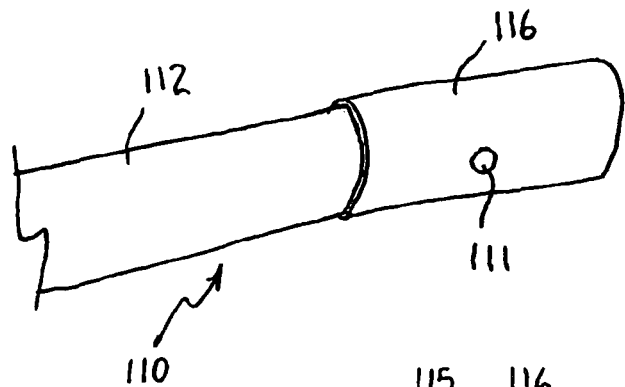
*Fig. 19*
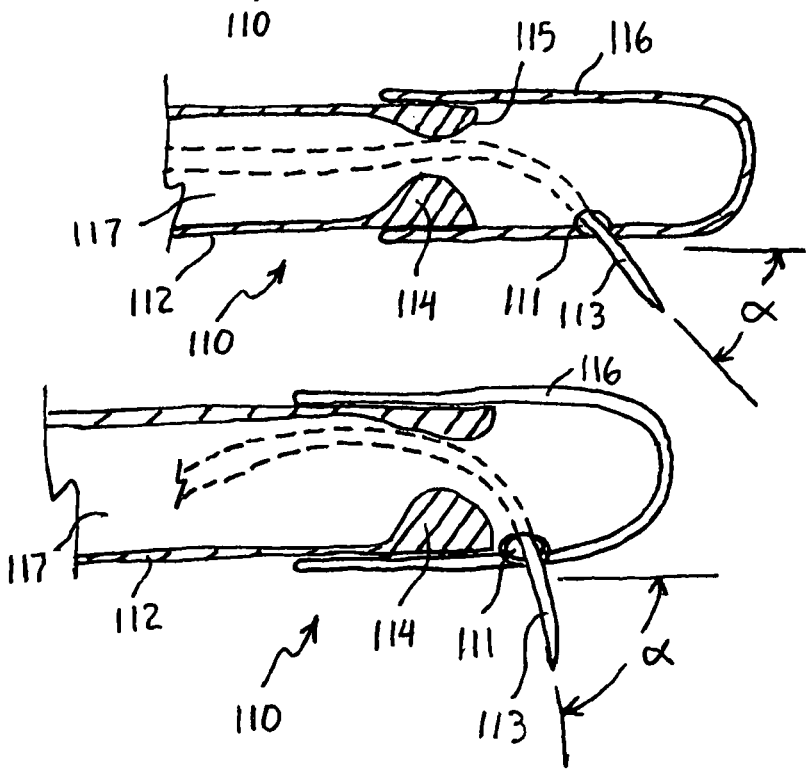
*Fig. 20*
*Fig. 21*
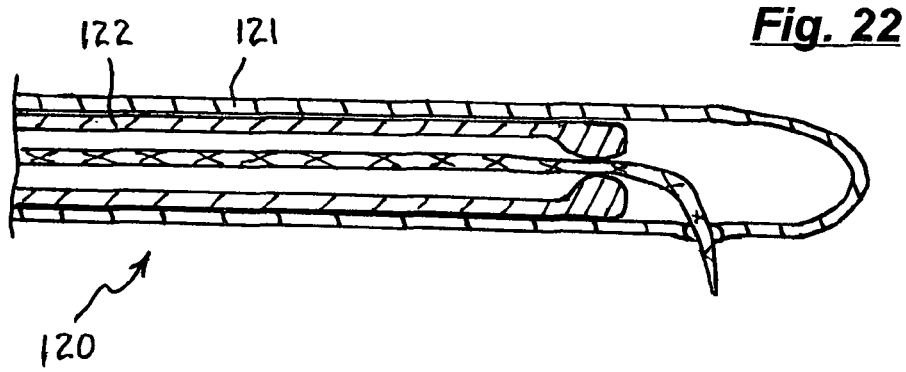
*Fig. 22*

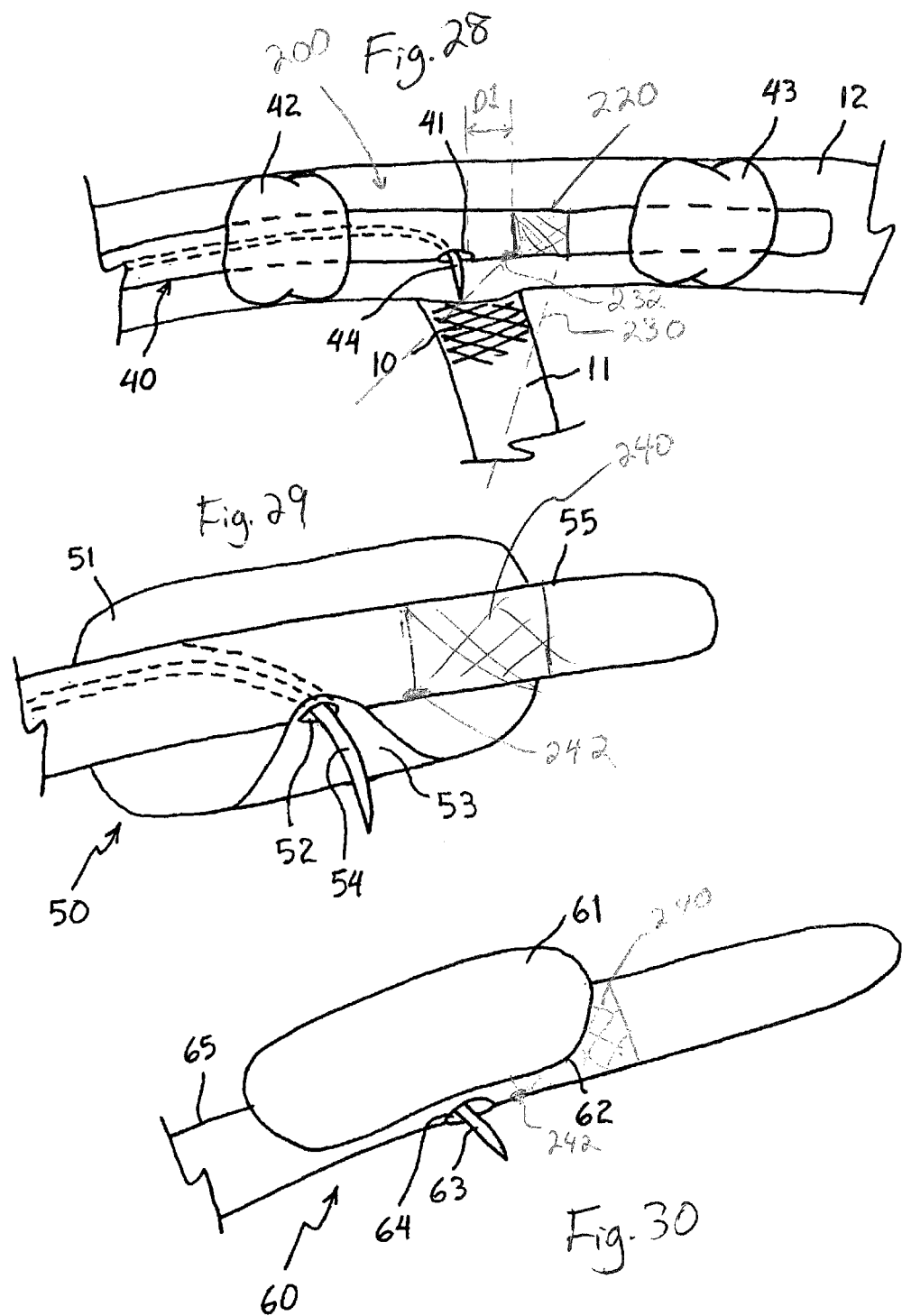

TELESCOPIC SIDE PORT CATHETER DEVICE WITH IMAGING SYSTEM AND METHOD FOR ACCESSING SIDE BRANCH OCCLUSIONS

RELATED APPLICATIONS

This application is a continuation-in-part of U.S. patent application Ser. No. 11/838,297 filed on Aug. 14, 2007, and claims priority of U.S. Provisional Application No. 60/837,900 filed on Aug. 14, 2006. The content of these prior applications are incorporated herein by reference.

BACKGROUND OF THE INVENTION

Field of the Invention

The present invention relates generally to catheters and methods of treating a stenosis of an artery. In particular, the present invention relates to catheters and methods for accessing chronic total occlusions (CTOs) in arteries caused by the buildup of arterial plaque tissue.

Description of the Related Art

Chronic total occlusion (CTO) is a condition where arterial plaque tissue grows to complete stenosis of an artery and prohibits blood flow. A CTO is formed by the agglomeration of three separate physiological materials: (i) cholesterol or fat, (ii) collagen or fibrous matter, and (iii) calcium-based deposits. A CTO is also often referred to as a functional occlusion.

There are two causal pathogenic phenomena often associated with the formation of a CTO. The first is the late development of an acute occlusion. The second is the progressive occlusion of a long-term high degree stenosis. Both involve a pre-existing plaque or thrombus to which the fat and fibrous material adhere, building up until a blockage of the blood vessel occurs. A CTO 10 will sometimes form in a side branch 11 of an artery 12 as shown in FIG. 1, which is difficult to access using conventional catheters and surgical techniques.

Physicians currently attempt to perforate CTOs 10 in side branches 11 using a stiff guide wire 13 as shown in FIG. 2. A small catheter 14 is used to position the guide wire 13 at the occlusion 10.

Another conventional technique involves the use of a curved catheter 15 to align a perforating guide wire 16 with the angle of the side branch 11, as shown in FIG. 3. One of the primary problems with this approach occurs when a compressive force is applied to the guide wire 16. The guide wire 16 must be pushed to perforate the occlusion 10 and as it is pushed, the catheter 15 in which the guide wire 16 is contained reacts in a negative manner, as shown in FIG. 4. As can be seen, the catheter 15 will be pushed and/or rotated away from the side branch 11, or misaligned with the side branch 11, as compressive force is exerted on the guide wire 16. The restraint offered by the catheter 15 is limited because it must be made of a material that is soft enough not to injure the arteries as it is advanced into the vascular system. Catheters are limited as to the amount of stiffness the catheter can contain before it will injure the artery as it is aligned with the side branch. In addition, the curvature of the catheter can cause substantial "whip" as a physician torques the catheter to align it with the side branch.

A compliant balloon 17 can be attached to the catheter 18 to help limit the reaction forces on the catheter 18, as shown in FIG. 5. The balloon 17 is inflated through a separate lumen in the catheter 18. The balloon 17 allows for more stability in the catheter 18 as it is used. However, it still suffers from the cantilever type positioning exhibited in FIG. 4. In addition, it is still subject to whip caused by the curvature of the catheter as torque is applied to position the catheter.

There is a need in the industry for improved devices and methods to assist surgeons in accessing CTOs in side branches of arteries.

SUMMARY

The present disclosure provides an occlusion crossing system utilizing an imaging system carried by the catheter to assist in guiding the advancement of the occlusion penetrating device.

In one aspect, the present disclosure provides a method of crossing an occlusion within a vessel. The method comprises positioning a catheter within a vessel of a patient, the catheter including an imaging element, a steering assembly and an occlusion crossing wire extendible through an exit opening in the catheter. The method includes advancing the imaging element through a main vessel to a position adjacent an occlusion of a side vessel and imaging the occlusion along with a portion of the side vessel. Once the vessel has been imaged, the catheter can be rotated to align the exit opening with the occlusion and the crossing wire can be advanced through the exit opening and into the occlusion. The steering assembly is operable to change the trajectory of the crossing wire.

In still a further form, the present disclosure provides a method of treating an internal structure within a patient. The method includes positioning a catheter adjacent a structure to be treated, the catheter including an imaging element, a steering assembly and a therapy delivery device extendible through an exit opening in the catheter, the steering assembly operable to adjust the trajectory of the therapy delivery device as it extends through the exit opening. The method includes advancing the imaging element to a position adjacent the structure to be treated, imaging the structure to be treated with the imaging element and aligning the exit opening with the structure to be treated. Once the exit opening is properly aligned, the therapy delivery device can be advanced through the exit opening and toward the structure to be treated. In one aspect, the trajectory of the therapy device can be controlled by the steering assembly while advancing the therapy delivery device.

In yet a further feature, the present disclosure provides a vessel occlusion crossing system. The system includes a catheter body having a lumen, an imaging element disposed on a distal portion of the catheter, a crossing wire slidably disposed within at least a portion of the catheter, and a steering assembly for changing the direction of the crossing wire after exit from the catheter body.

These and other aspects of the present disclosure will become apparent from the following detailed description and associated drawings.

BRIEF DESCRIPTION OF THE DRAWINGS

The present invention will become more clearly appreciated as the disclosure of the present invention is made with reference to the accompanying drawings. In the drawings:

FIG. 8 shows another embodiment of the present invention in which support balloons are used to stabilize the catheter during usage.

FIGS. 9 and 10 show another embodiment of the present invention in which a single support balloon is centered over the side port and attached to the catheter shaft at the proximal and distal ends of the balloon and around the side port.

FIG. 11 shows another embodiment of the present invention in which a "hot dog bun"-shaped balloon is centered about the side port and attached to the catheter shaft.

FIG. 12 shows another embodiment of the present invention in which two lumens are provided in the catheter; one lumen leading to the side port and the other lumen providing a passage for inflating support balloons attached to the catheter.

FIGS. 13 and 14 are side and end views of another embodiment of the present invention in which a channel is provided for inserting the catheter over a guide wire previously placed in the non-occluded artery.

FIGS. 19 to 21 show another embodiment of the present invention in which the side port is movable relative to the base catheter to change the angle at which the guide wire exits the catheter.

FIG. 22 shows another embodiment of the present invention in which telescoping sleeves are used to change the angle at which the guide wire exits the catheter.

FIG. 28 illustrates a first embodiment of an occlusion crossing system incorporating an imaging system.

FIGS. 29 and 30 illustrate a further embodiment of an occlusion crossing system incorporating an imaging system.

FIG. 34 illustrates a display device displaying an image associated with the imaging system.

DETAILED DESCRIPTION OF THE INVENTION

Side port catheters and methods for accessing side branch occlusions in arteries according to the present invention will now be explained in detail with reference to the accompanying drawings.

Figure 1:
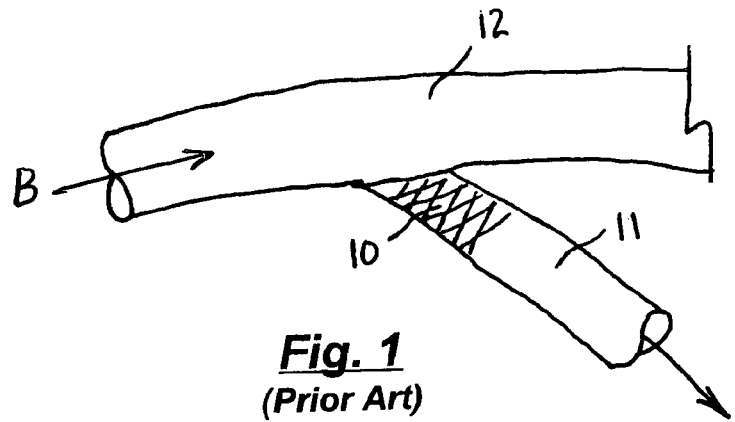
FIG. 1 shows a vessel in a coronary vascular system with a side branch that is totally occluded.
Figure 2:
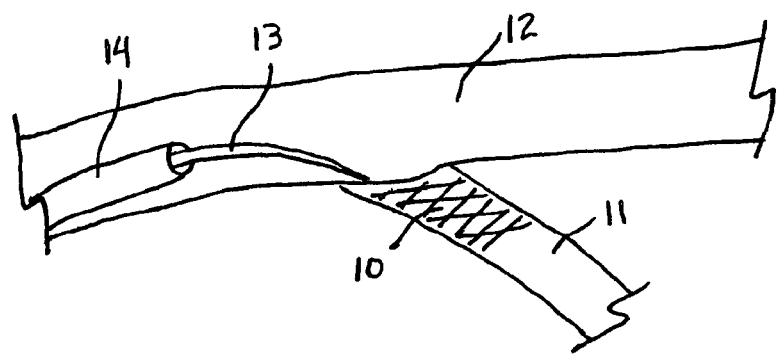
FIG. 2 shows a conventional technique used to perforate an occlusion with a stiff guide wire and a small catheter to position the guide wire at the occlusion.
Figure 3:
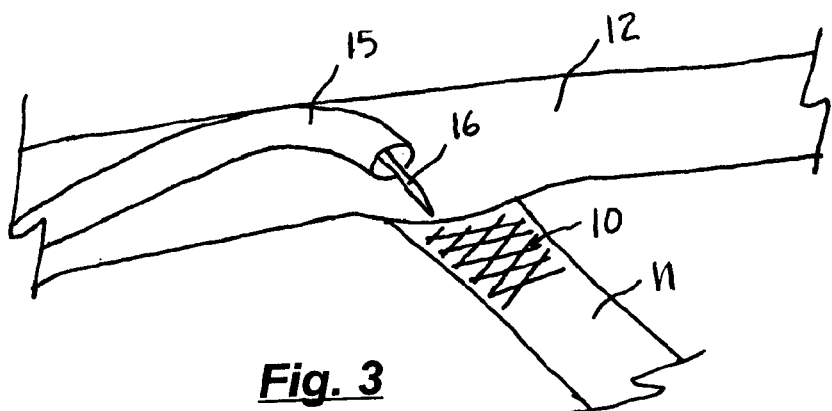
FIG. 3 shows a conventional technique that uses a curved catheter and/or curved catheter/guide wire combination to align the perforating guide wire with the angle of the side branch.
Figure 4:
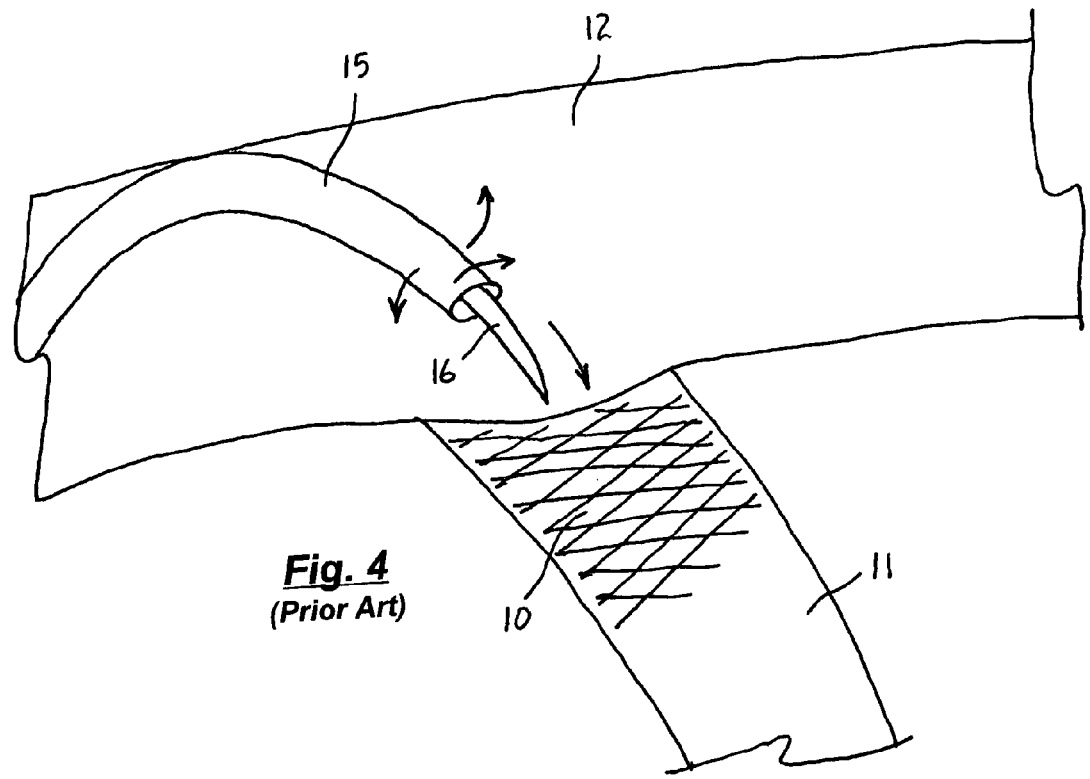
FIG. 4 illustrates the reactive forces on the catheter when the guide wire is pushed to perforate the occlusion using the conventional technique.
Figure 5:
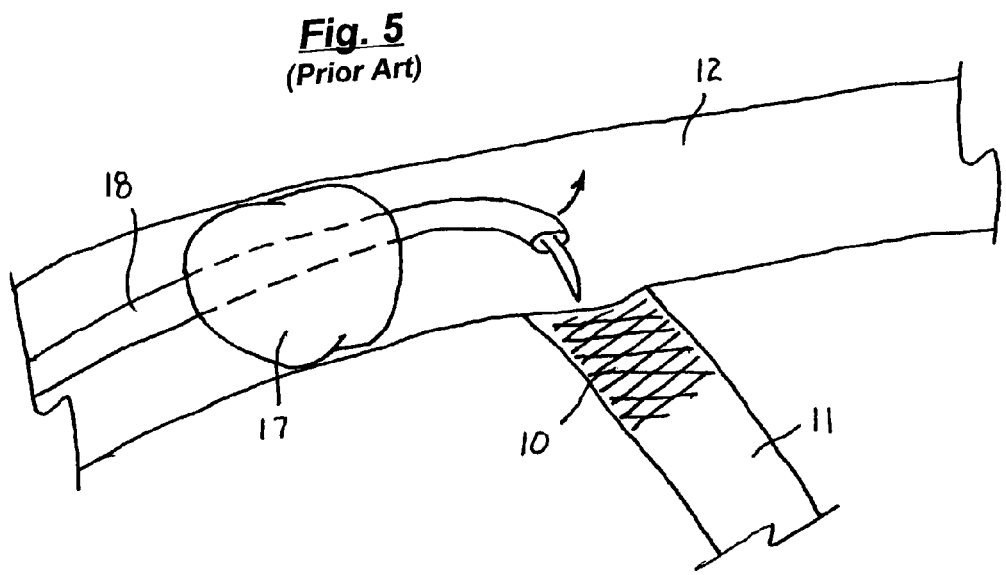
FIG. 5 shows a catheter with a balloon attached to help limit the reaction of the catheter as the guide wire is pushed into the occlusion.
Figure 6:
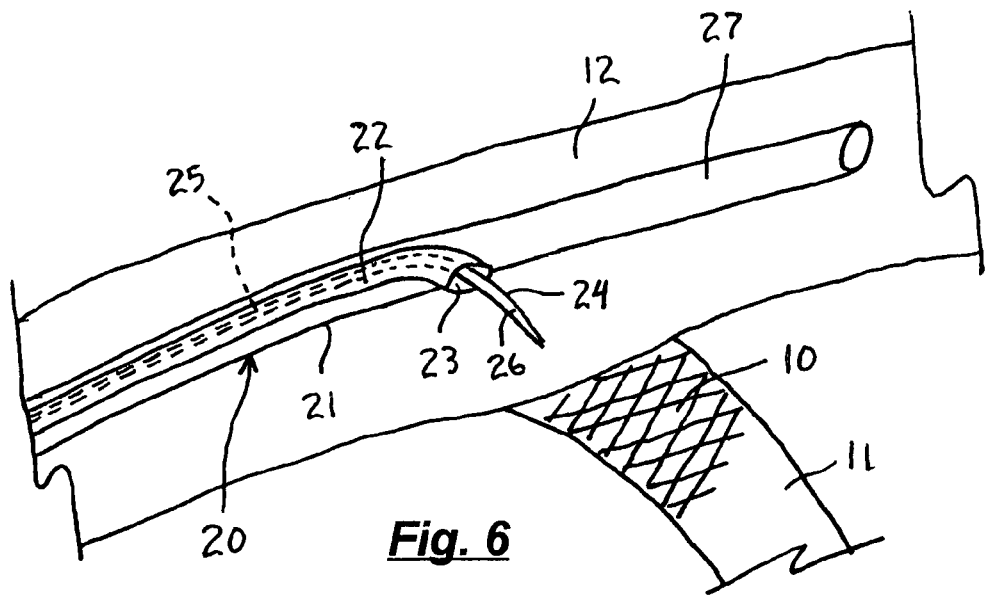
FIG. 6 shows a catheter according to an embodiment of the present invention having a side port through a sidewall for delivering a guide wire to a side branch occlusion in an artery.

FIG. 6 shows a catheter 20 having a sidewall 21 and an internal lumen 22. A side port 23 is formed through the sidewall 21 of the catheter 20. A perforating guide wire 24 is provided in the catheter 20 for accessing and treating a side branch occlusion 10 in an artery 12. The guide wire 24 has a proximal portion 25 within the internal lumen 22 of the catheter 20 and a distal portion 26 arranged to be movable out of the side port 23. The side port 23 is arranged to bend the guide wire 24 away from a longitudinal axis of the catheter 20 as the guide wire 24 passes through the side port 23. The guide wire 24 can thus be delivered through the side port 23 to the occlusion 10 in the side branch 11 of the artery 12.

In FIG. 6, a distal portion 27 of the catheter 20 extends for some distance past the side port 23 to add stability to the catheter 20 while the guide wire 24 is being delivered through the side port 23. The perforating guide wire 24 may be either straight or formed with a pre-curved tip at its distal portion 26. If a curved tip guide wire 24 is used, the guide wire 24 will be held straight within the lumen 22 of the catheter 20 until the distal portion 26 of the guide wire 24 exits through the side port 23. The length of the catheter 20 will help stabilize the catheter 20 as the curved guide wire 24 is pushed through the catheter 20. If a straight guide wire is used, the guide wire 24 must be flexible enough to deflect and bend as it enters the curvature contained within the catheter 20 to deflect the guide wire 24 out of the side port 23.

The catheter 20 with the side port 23 shown in FIG. 6 will torque with very little "whip" and allow for relatively easy positioning of the side port 23. The compressive force of the guide wire 24 necessary to deflect it through the side port 23 will result in a tensile loading on the catheter shaft that is fairly easy to restrain.

Figure 7:
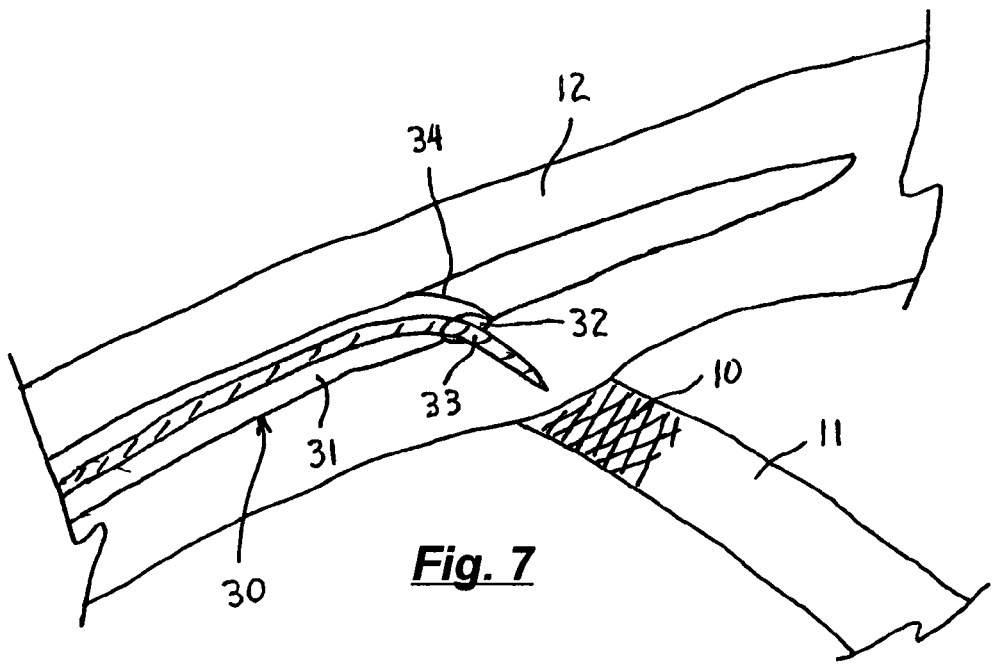
FIG. 7 shows another embodiment of the present invention in which the catheter contains a single lumen and side port through which the guide wire is passed.

FIG. 7 shows an embodiment of a catheter 30 in which the catheter contains a single lumen 31 and side port 32 through which the guide wire 33 is passed. The single lumen 31 truncates at its distal end 34 to the side port 32 to guide the guide wire 33 to the opening of the side port 32.

FIG. 8 shows an embodiment of a catheter 40 with a side port 41 in which one or more support balloons 42, 43 are used to stabilize the catheter 40 during delivery of the guide wire 44 through the side port 41. A first balloon 42 can be positioned proximal of the side port 41, and a second balloon 43 can be positioned distal of the side port 41.

FIGS. 9 and 10 show an embodiment of a catheter 50 in which a single support balloon 51 surrounds the catheter 50 adjacent to the side port 52 and has a recess 53 in the support balloon 51 to allow delivery of the guide wire 54 through the side port 52. In this case, the balloon 51 can be centered over the side port 52 and attached to the outer sleeve 55 of the catheter 50 at the proximal and distal ends of the balloon 51 and around the side port 52.

FIG. 11 shows an embodiment of a catheter 60 in which a balloon 61 having a general shape of a hotdog bun is used for stabilizing the catheter 60. In this embodiment, the balloon 61 has an open side 62 for allowing delivery of the guide wire 63 through the side port 64. The balloon 61 can be centered about the side port 64 and attached to the outer sleeve 65 of the catheter 60 as shown.

FIG. 12 shows an embodiment of a catheter 70 in which two lumens 71, 72 are provided in the catheter. The first lumen 71 serves as the lumen for delivering the guide wire to the side port 73, and the second lumen 72 serves as a balloon inflation lumen for delivering gas or fluid to a balloon inflation port 74 for inflating the support balloon or balloons after insertion of the catheter 70 into a patient.

FIGS. 13 and 14 show an embodiment of a catheter 80 in which an insertion lumen 81 is provided for inserting the catheter 80 over a second guide wire 82 previously placed in the non-occluded portion of the artery 12. The second guide wire 82 can pass through the insertion lumen 81 for guiding the catheter 80 into position within a patient's body. As shown in FIG. 13, the insertion lumen 81 is open at both its distal and proximal ends 83, 84 and arranged so that the balloon and the balloon inflation port 85 and the side port 86 of the catheter 80 are located between the distal and proximal ends 83, 84. The insertion lumen 81 passes through the inflation lumen 87 of the catheter 80.

Figure 15:
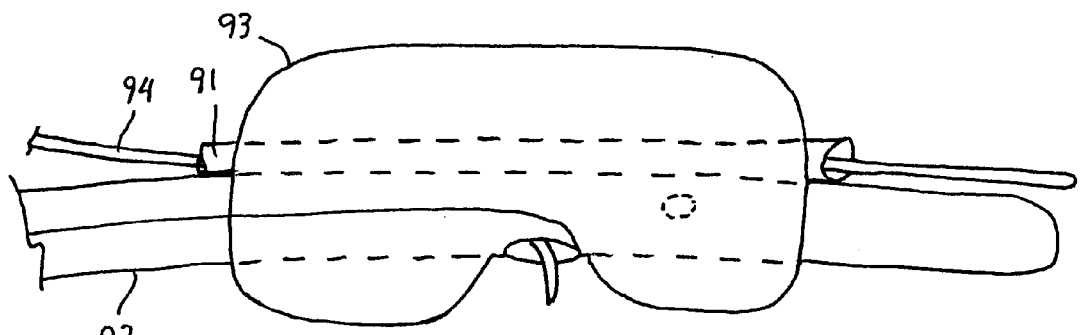
FIGS. 15 and 16 are side and end views of another embodiment of the present invention in which a guide wire lumen is provided on the exterior of the primary catheter with a support balloon.
Figure 16:
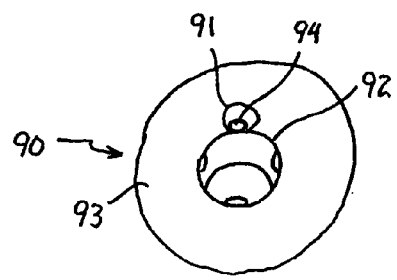
Figure 17:
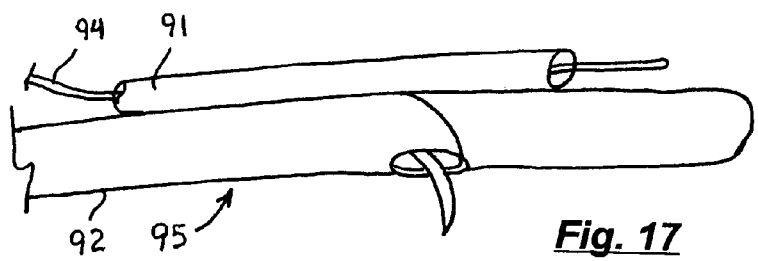
FIG. 17 shows another embodiment of the present invention in which a guide wire lumen is provided on the exterior of the primary catheter without a support balloon.

FIGS. 15 and 16 show an embodiment of a catheter 90 in which a tubular member 91 is provided on the exterior of the primary catheter 92. The tubular member 91 provides an insertion lumen for a second guide wire 94 used to guide the catheter 90 into position within a patient's body. In this embodiment, a support balloon 93 surrounds both the tubular member 91 and the primary catheter 92. FIG. 17 shows a similar embodiment of a catheter 95, except that no support balloon is used.

Figure 18:
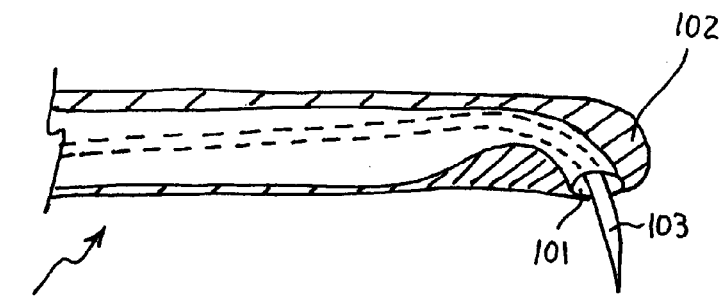
FIG. 18 shows another embodiment of the present invention in which no extension of the catheter extends past the side port, and a molded tip is provided to facilitate movement of the exiting guide wire.

FIG. 18 shows an embodiment of a catheter 100 in which no extension of the catheter extends past the side port 101. In this embodiment, a molded tip 102 is provided to facilitate movement of the exiting perforating guide wire 103.

FIGS. 19 to 21 show another embodiment of a catheter 110 in which the side port 111 is movable relative to the base portion 112 of the catheter 110 to change the angle □ at which the guide wire 113 exits the catheter 110. In this embodiment, the base portion 112 of the catheter 110 has a molded internal guide 114 within its tip 115, and a movable portion 116 in which the side port 111 is formed. The base portion 112 and movable portion 116 are telescoping members that can be adjusted relative to one another. As the side port 111 on the movable portion 116 is positioned relative to the base portion 112, the angle □ of the guide wire 113 exiting the catheter 110 will change. In other words, the movable portion 116 can be moved relative to the base portion 112 to adjust the angle □ of the guide wire 113 exiting the catheter 110. The relative positions of the movable portion 116 and the base portion 112 can be adjusted during a surgical procedure using a push/pull wire or by applying a fluid pressure within a lumen 117 of the base portion 112. Support balloons and the like as described above can be incorporated into this embodiment as desired.

FIG. 22 show an embodiment of a catheter 120 in which telescoping sleeves 121, 122 are used to change the angle □ at which the guide wire 113 exits the side port 111 of the catheter 110. The telescoping sleeves 121, 122 will provide a convenient means by which a surgeon can adjust the relative positions between the outer "movable" portion 121 and the inner "base" portion 122 of the catheter 120 from the proximal end of the catheter 120.

Figure 23:
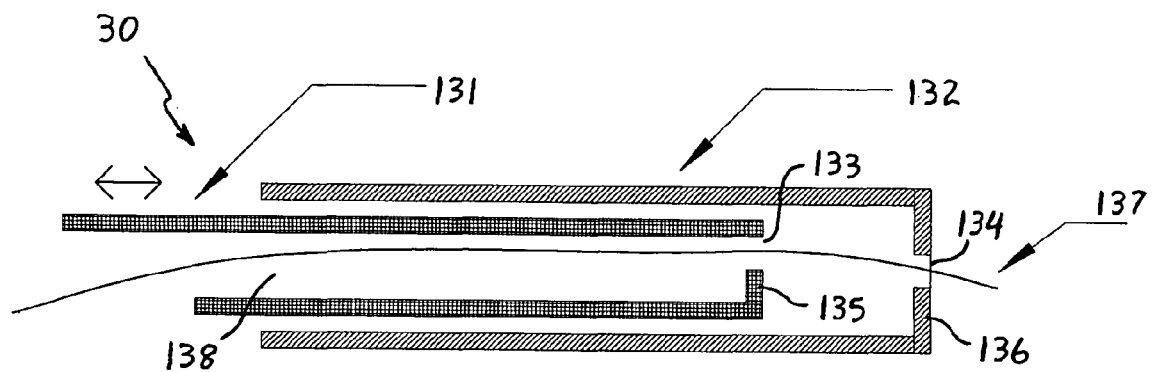
FIG. 23 shows another embodiment of the present invention in which telescoping inner and outer tubes having offset ports at their distal ends are used to change the angle at which the guide wire exits the catheter.
Figure 24:
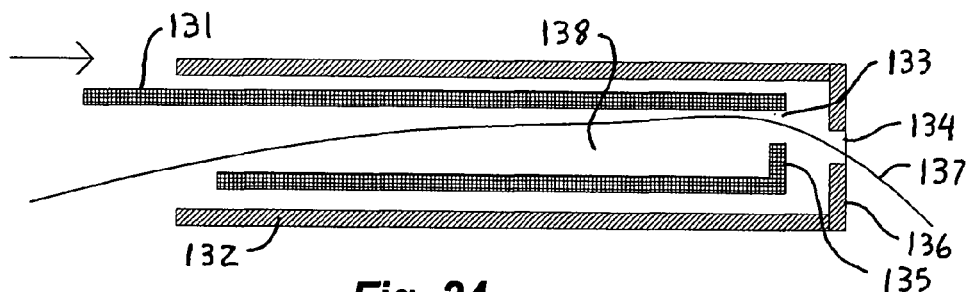
FIGS. 24 and 25 show the catheter of FIG. 23 with the inner tube at different positions relative to the outer tube to cause the guide wire to exit the catheter at different angles.
Figure 25:
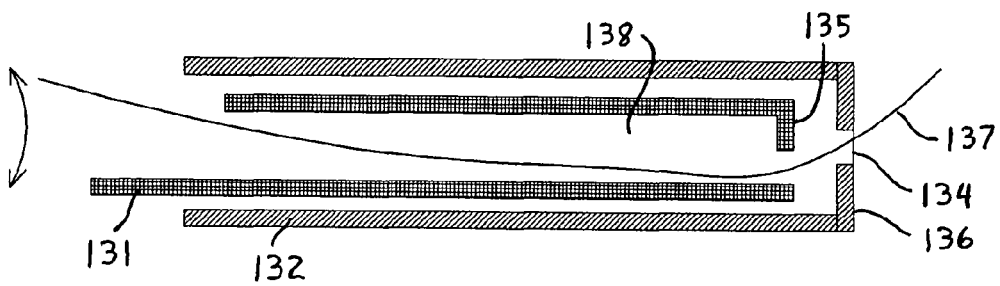

FIGS. 23 to 25 show another embodiment of a catheter 130 in which telescoping inner and outer tubes 131, 132 having offset ports 133, 134 at their distal ends 135, 136 are used to change the angle at which the guide wire 137 exits the catheter 130. The inner and outer tubes 131, 132 are arranged for rotational and/or telescoping movement relative to each other. For example, the inner tube 131 can be moved in a telescoping manner relative to the outer tube 132 from the position shown in FIG. 23 to the position shown in FIG. 24. Further, the inner tube 131 can be moved in a rotational manner relative to the outer tube 132 from the position shown in FIG. 24 to the position shown in FIG. 25.

Figure 26:
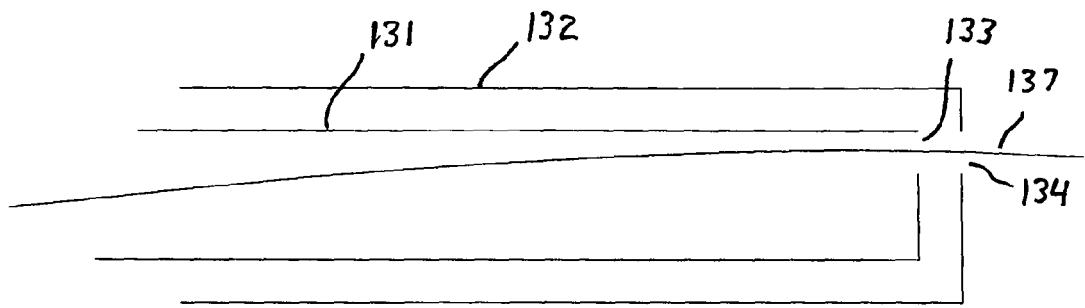
FIGS. 26 and 27 show another variation of the catheter of FIG. 23 in which the exit port of the outer telescoping tube is offset from the longitudinal axis of the catheter.
Figure 27:
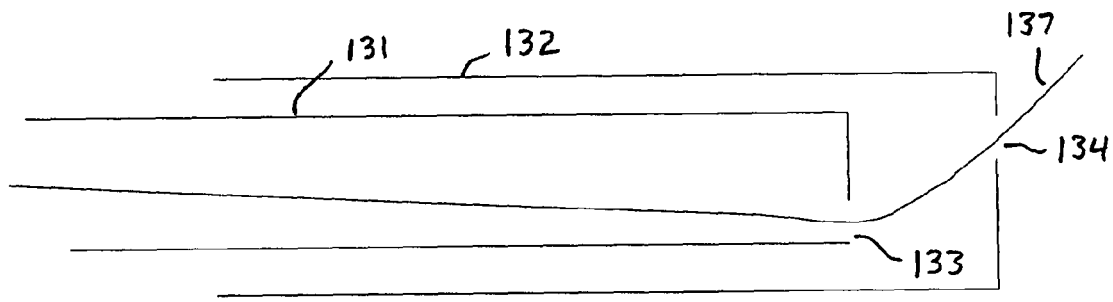

The inner tube 131 has an internal lumen 138 that leads to the first port 133 at the distal end 135 of the inner tube 131. The outer tube 132 has the second port 134 at the distal end 136 of the outer tube 132. In the embodiment shown in FIGS. 23 to 25, the first port 133 is offset from the longitudinal axis of the catheter 130, and the second port 134 is approximately concentric with the longitudinal axis. In the embodiment shown in FIGS. 26 and 27, both the first and second ports 133, 134 are offset from the longitudinal axis of the catheter. In both embodiments, the first and second ports 133, 134 are offset relative to each other so that relative movement between the inner and outer tubes 131, 132 will cause relative movement between the first and second ports 133, 134 to adjust an angle of the perforating guide wire 137 exiting the catheter.

In the catheter embodiments shown in FIGS. 23 to 27, the degree of deflection of the guide wire 137 can be increased or decreased by telescoping the tubes 131, 132, and/or by rotating one or both tubes 131, 132 to change the alignment of the first and second ports 133, 134. The catheter 130 can also be used in combination with an inflatable stabilizing balloon as described above in connection with the other embodiments disclosed herein.

Catheter devices according to various embodiments of the present invention have been described above. Methods of using these catheter devices to access a side branch 11 of an artery 12 will now be described.

The basic method includes a first step of providing a catheter 20 having a sidewall 21 and an internal lumen 22, a side port 23 formed through the sidewall 21, and a perforating guide wire 24 positioned within the internal lumen 22. A second step is to deploy the catheter 20 to a location with the side port 23 suitably aligned with a side branch 11 of an artery 12 to be accessed. A third step is to move the guide wire 24 through the side port 23 and into the side branch 11 of the artery 12.

In the catheter embodiments having a distal portion 27 that extends past the side port 23, the method will include the step of positioning the distal portion 27 on a distal side of the side branch 11 of the artery 12 to stabilize the catheter 20 while the guide wire 24 is being delivered through the side port 11.

In the catheter embodiments having one or more balloons 42, 43 attached to the catheter, the method may include the further step of inflating the balloon 42, 43 within the artery 12 to stabilize the catheter while the guide wire 44 is being delivered through the side port 41. As described above, a first balloon 42 can be positioned proximal of the side port 41 and a second balloon 43 can be positioned distal of the side port 41.

In the catheter embodiments having an insertion lumen 81, the method may include the further step of guiding the catheter within a patient's body over a second guide wire 82 that passes through the insertion lumen 81. As described above, the insertion lumen 81 has open distal and proximal ends 83, 84 and is arranged so that the side port 86 of the catheter is located between the distal and proximal ends 83, 84.

In the catheter embodiments having a base portion 112 and a movable portion 116 with the side port 111 formed in the movable portion 116, the method may include the further step of moving the movable portion 116 relative to the base portion 112 to adjust an angle □ of the guide wire 113 exiting the catheter.

Referring now to FIG. 28, there is shown an alternative embodiment of a catheter assembly according a further aspect of the present disclosure. The embodiment 200 retains all of the features of FIG. 8 described in detail above, but further includes an on-board imaging system 220. The imaging system is spaced distally by a distance D1 from the sidewall opening 41. In one aspect, D1 can vary from about 1 mm to about 1 cm depending on the desired spacing which may be a function of space constrains within the catheter and the desired imaging angle of the field of view illustrated by dashed lines 230. Typically, the field of view will be oriented between 90 and 45 degrees outwardly from the catheter side wall such that the expected side branch or tissue of interest will be within the primary field of view when deployed within a vessel. As illustrated, a marker element 232 is positioned within the field of view of the imaging system 220 radially aligned about the longitudinal axis to be in alignment with the sidewall opening 41. As shown in more detail with respect to FIGS. 32-34, the marker element 232 provides a visual indication, during imaging, of the orientation of the sidewall opening with respect to surrounding tissue structures and the images viewed on a display screen. Referring now to FIGS. 29 and 30, the catheter system previously described with respect to FIGS. 9-11 has been enhanced to include an on-board imaging system 240. As previously discussed, the system include a visualization marker 242 radially aligned at the some radial or angular location about the longitudinally axis of the catheter, but offset longitudinally, from the side wall opening 64. The imaging systems 220 and 240 may be used to locate the area of interest prior to balloon inflation. Once the area is identified, the balloons of FIG. 28 or the single balloon of FIG. 29 can be inflated to maintain the catheter system in a fixed location allowing the imaging system to monitor the occlusion 10 while deploying the crossing wire. The balloon systems may be particularly useful for optical imaging systems as the blood in the vessel may be displaced by a fluid, such as saline, distal of the balloons for better imaging.

Figure 31:
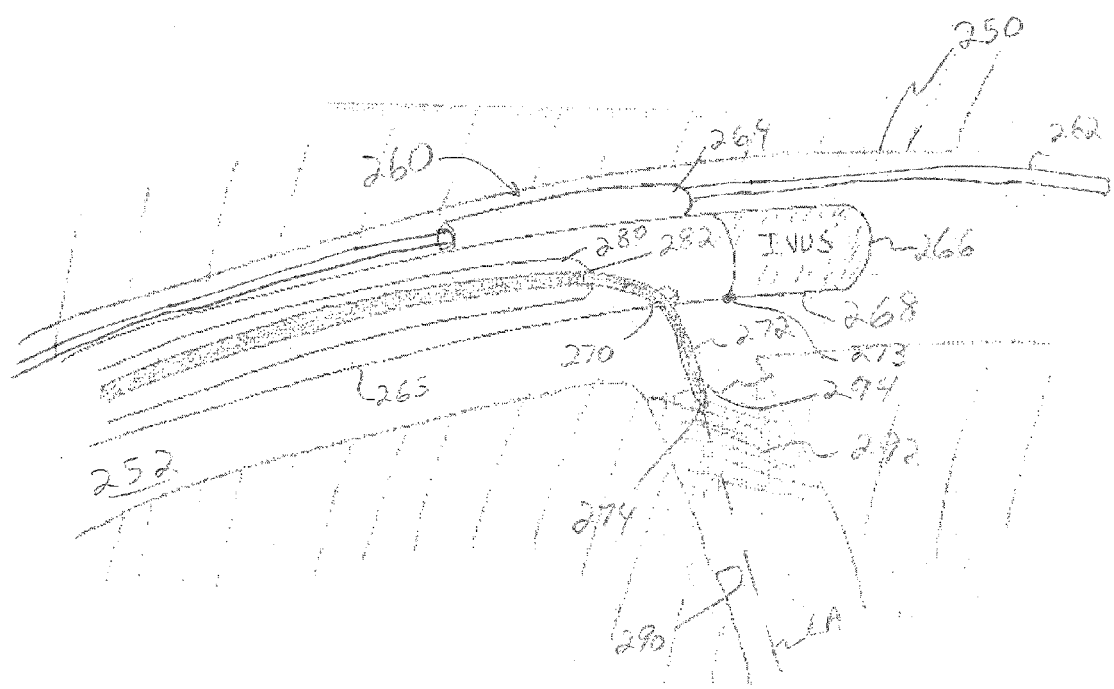
FIGS. 31-33 illustrate still a further embodiment an occlusion crossing system incorporating an imaging system.

Referring now to FIG. 31, there is shown still a further embodiment of a treating catheter incorporating a steerable crossing wire assembly with an on-board imaging system positioned to aid in the deployment and navigation of the crossing wire as it is extended outside of the delivery catheter. The treating catheter 260 is deployed within the lumen 252 of primary vessel 250. The treating catheter 260 is shown after having been positioned on guide wire 262 by use of the monorail assembly 264. The distal tip 266 containing imaging system 268 has been positioned slightly beyond side branching vessel 290. The imaging system 268 has been used to locate the position of the side branching vessel 290 containing an occlusion 292 and has been oriented such that visual marker 273 is oriented to radially align with the side branching vessel 290. As illustrated, the visual marker is aligned with the side wall opening 270. Thus, the crossing wire 272 can be manipulated by the steering catheter 280 to exit the side wall opening 270 adjacent the side branching vessel 290. As explained more fully above, movement of the steering catheter 280 within the delivery catheter 265 changes the position of the opening 280 with respect to opening 270 such that the crossing wire 272 is effectively guided as it exits the delivery catheter. As shown in FIG. 31, the steering mechanism is moved within the delivery catheter to position the tip 274 of the crossing wire 272 in contact with the surface 294 of the occlusion 92.

Figure 32:
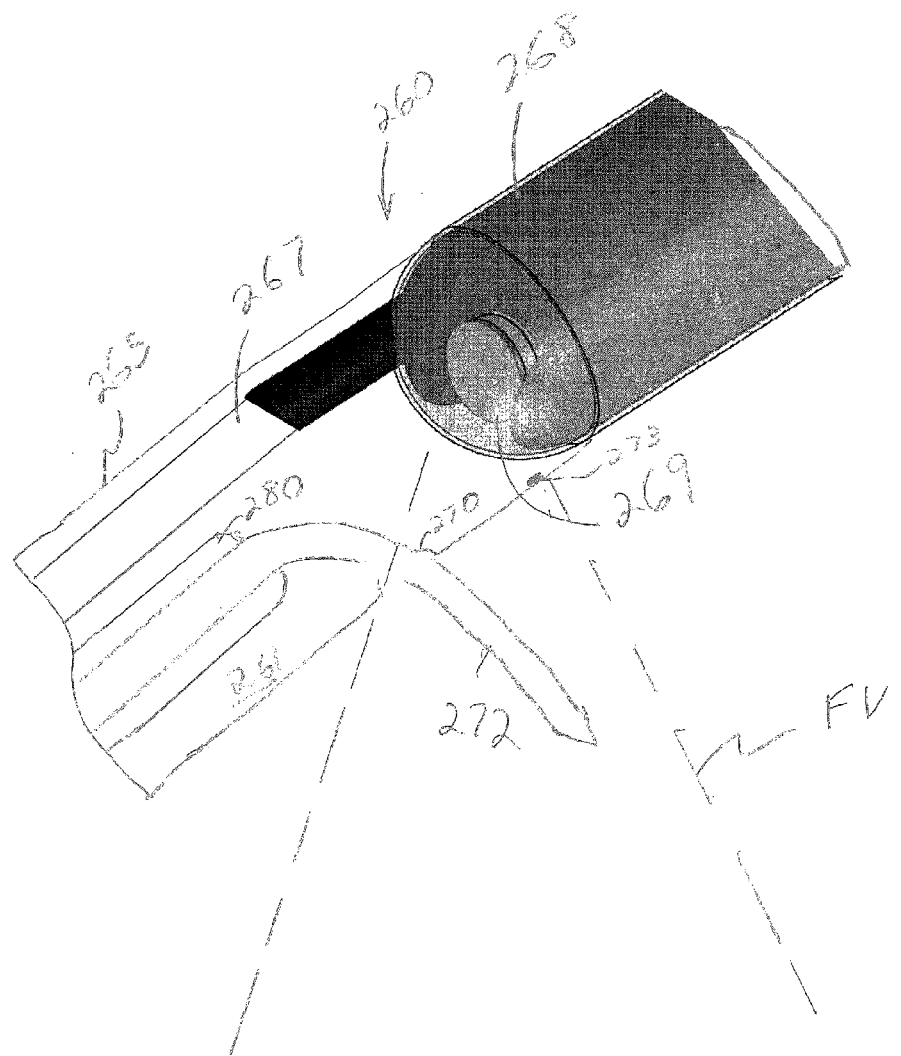

Referring now to FIG. 32, there is shown a partial cross sectional diagrammatic view of the treating system 260 incorporating an oscillatory imaging system 268. The oscillatory imaging system 268 utilizes a single transducer 269 that is oscillated through an arc of between 120 and 360 degrees to form an image. Cable 267 provides power to drive the oscillation and carry signals to and from the ultrasound transducer 269. In the illustrated embodiment, the arc defines a field of view FV that is angled backwards toward the opening 270 such that the field of view FV encompasses tissue disposed radially outward from the opening 270. As discussed above, a marker 273 is positioned on the catheter (or within a component of the imaging system) within the field of view such that when the field of view is output on a display device a user can determine the orientation of the marker 273 and aligned opening 270 in relation to the imaged tissue surrounding the catheter.

Figure 33:
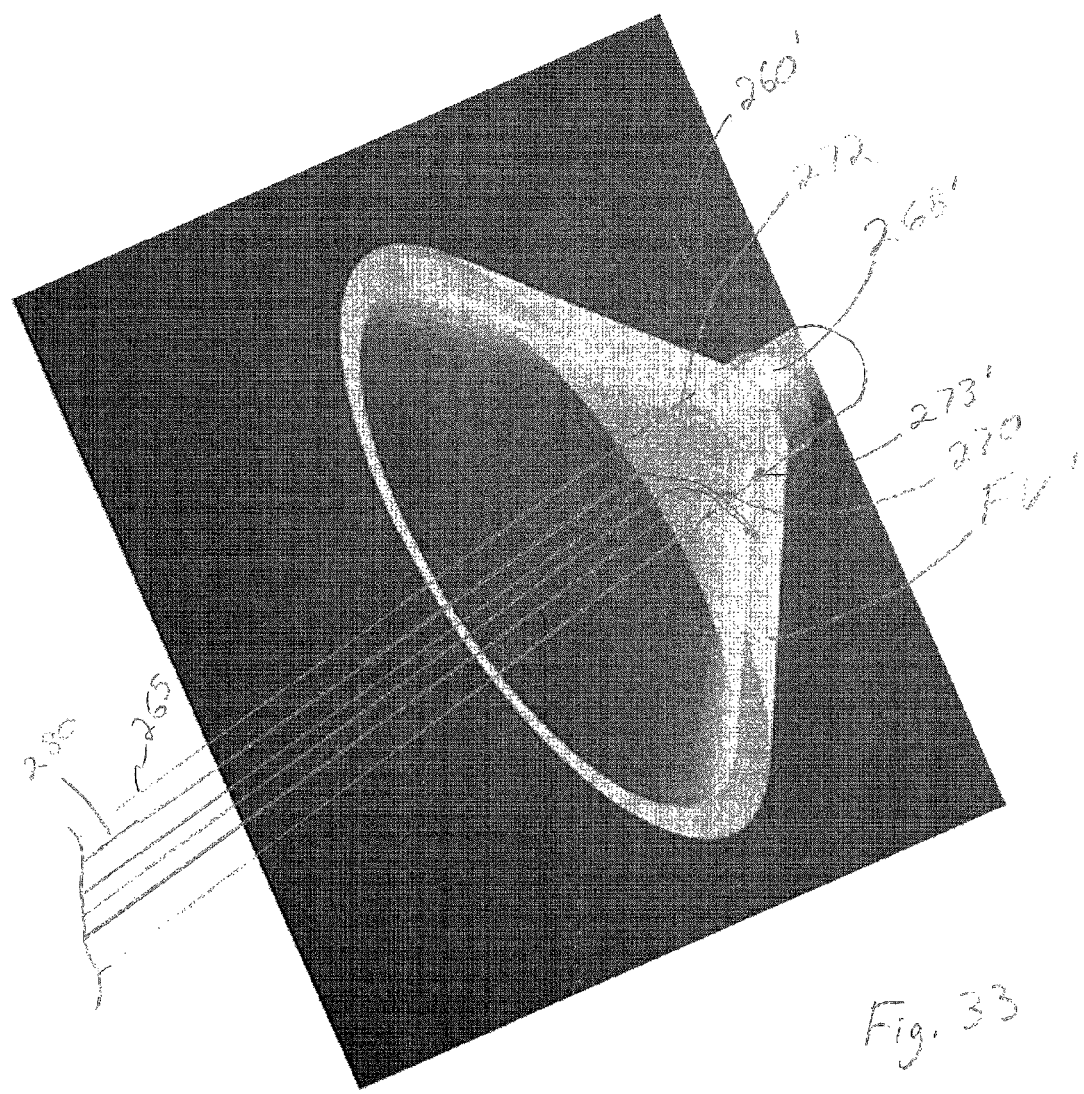
Figure 37:
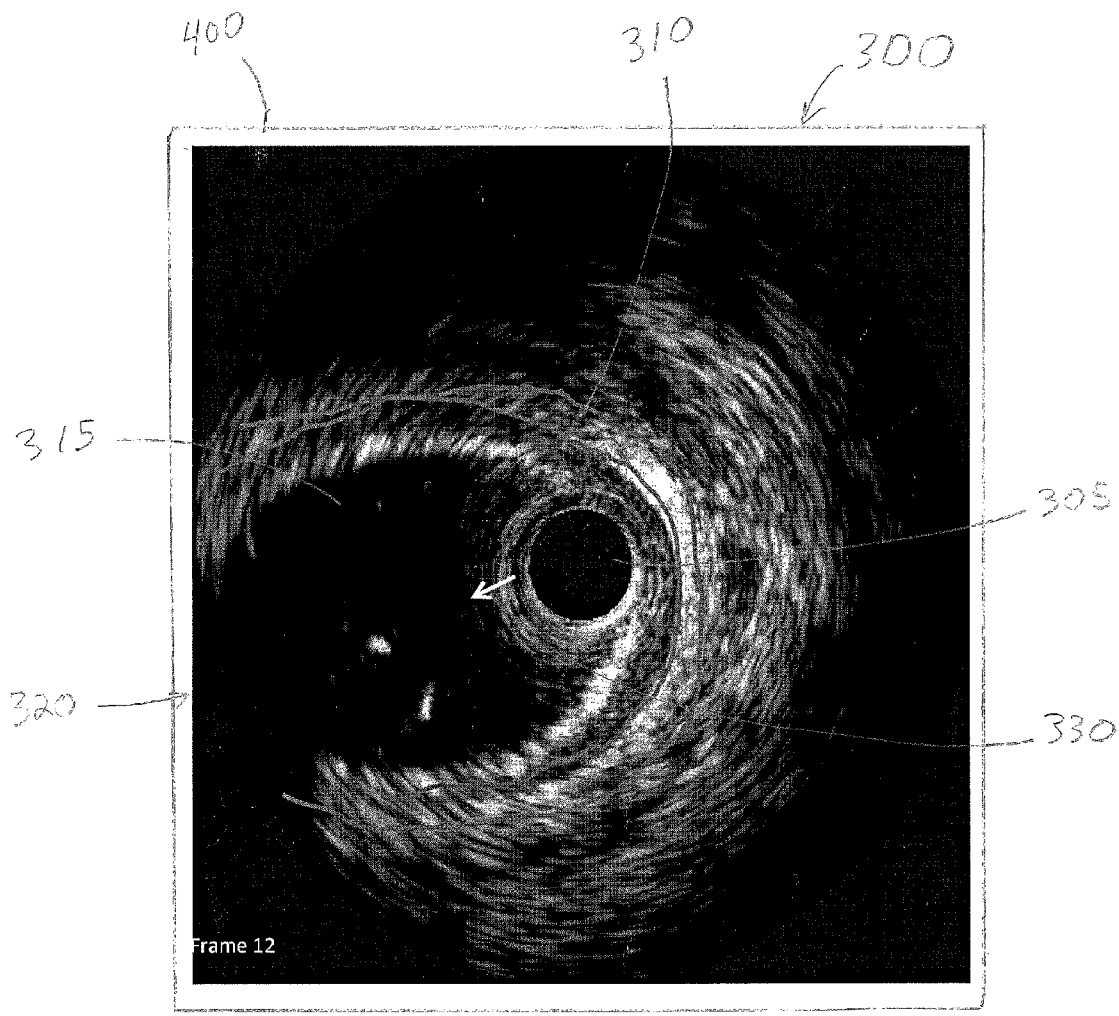

Referring now to FIG. 33, there is shown still a further embodiment of a treating system 260' having an alternative imaging system 268'. The crossing wire steering components of the system are the same as set forth above. In the illustrated embodiment, the imaging system 268' is a 360 degree imaging system that has a field of view that includes all tissue surrounding the catheter in a 360 degree revolution. Exemplary solid-state IVUS systems usable as the imaging system 268', also referred to as phased-array imaging systems, are described, for example, in U.S. Pat. No. 6,283,920 and U.S. Pat. No. 6,283,921, each of which is incorporated herein by reference in their entirety. Such solid-state systems typically have lower resolution but higher depth of penetration than rotational systems. Although the imaging system may utilize a field of view oriented at 90 degrees from the catheter, as shown in FIG. 33, the exemplary field of view FV' has been angled rearward at an angle of approximately 45 degrees to define a conical field of view. The field of view FV' includes a visual marker 273' aligned with opening 270. In an alternative aspect, the imaging system 268' could include a single imaging element continuously rotated about an axis.

Referring now to FIG. 34, there is shown an example of a display device 400 showing a display 300 outputting a field of view FV' from the imaging system 268'. The image 300 illustrates a position of the imaging device at location 305, primary lumen 252 of the vessel at 315, side branching vessel lumen 290 at location 320 and visual marker 273' at the location designated by arrow 300. As illustrated, the arrow 330 points the direction that the crossing guide wire 272 will be exiting opening 270. Thus, the user can use the visual marker 330 to align the side opening 270 with the branching side vessel 290 as shown in FIG. 34.

As a further feature, the sensed image data received from imaging system 268' may be further processed by a tissue characterization system. In one feature, the system may identify and display lumen or vessel wall boundaries illustrated by lines 310 on the image 300, along with determining the tissue characteristics of the occlusion 292. In still a further feature, tissue characterization may be used to identify adventitial tissue to alert the user of the location of the adventitial tissue to prevent unwanted penetration outside of the vessel wall. A system and method of adventitial tissue characterization is disclosed in U.S. Patent Application Ser.

No. 61/784,570 filed Mar. 14, 2013, entitled: SYSTEM AND METHOD OF ADVENTIAL TISSUE CHARACTERIZATION, incorporated by reference herein in its entirety.

Alternatively, the occlusion crossing guide wire may be replaced with a treatment device such as an ablation electrode or a suturing device. It will be appreciated that with alternative treatment devices steered with the control system described herein as aided by the above described imaging system, that ablation therapies and structural heart repairs maybe accomplished with precision using the combination of mechanical steering control and on-boarding imaging adjacent the treatment device.

The above described imaging systems have been illustrated utilizing an ultrasound imaging system as an example. However, these examples are provided only for the purpose of illustration and the present concepts are not limited to the type of imaging system utilized. Any type of imaging system may be incorporated with the mechanical steering system described above including, for example, but without limitation, optical systems, optical coherence tomography (OCT), photoacoustic sensors, optical IVUS, and spectroscopy.

A specific method of using the treating system 260 will be described below, although any of the treating systems disclosed above can be modified to incorporate an imaging system as described and used in a similar manner. Referring to FIG. 31, as an initial step, a guide wire 262 is positioned in the primary vessel 252 and the treating system 260 is advanced along the guide wire until it is positioned in the area of the occluded side branching vessel 290. As shown in FIG. 34, the imaging system may be moved along the guide wire until the field of view displays an image illustrating a side branching vessel. Once the side branching vessel has been identified, the treating system catheter 260 is rotated until the visual marker 273 (as indicated by the marker 330 on the display) is aligned with the side branching vessel (as indicated by region 320 on the display). Once properly aligned, a user may move the treating device longitudinally along the guide wire to determine the width of the opening of the side branching vessel and its location relative to the distance D1 between the side wall opening 270 and the imaging system 268. Once the opening 270 has been rotationally oriented and longitudinally oriented to be disposed adjacent the side branch 290, the steering catheter 280 is manipulated within the delivery catheter with respect to opening 270 to change the orientation and/or trajectory of the longitudinal axis LA of crossing wire 270 as it exits opening 270. As shown in FIG. 31, the longitudinal axis LA is oriented to extend across the occlusion 292 without penetration side walls of the vessel 290. As described above, the imaging system 268 can be used to identify boundaries of the vessel 290 along with using tissue characterization to determine the tissue type of the material making up the occlusion 292. In this manner, the crossing wire can be safely guided across the occlusion. Once a safe path is identified, the crossing wire 272 can be advanced into and across the occlusion 292. During advancement of the crossing wire 272, the imaging system may be continuously activated so that the position of the crossing wire 272 in relation to the vessel 290 is constantly monitored in real time. The monitoring may include observation of the actual location of the crossing wire as well as a projection of the expected path or trajectory of the crossing wire to avoid inadvertently passing through or otherwise perforating the lumen of the vessel. In some applications, such as subintimal tracking, the imaging system may be utilized to characterize vessel tissue and/or identify borders between vessel wall tissue segments. For example, the imaging system provides display information to the user identifying the boundary of the intima. The user may then use the steering assembly to orient the alignment of the crossing wire to extend along a subintimal path. The process of displaying, identifying and aligning the crossing wire to remain in the subintimal path continues until the crossing wire has been advanced beyond the occlusion. Once beyond, the occlusion as indicated by the imaging system, the steering mechanism can be actuated to cause the crossing wire to change orientations such that further advancement penetrates the intimal tissue and re-enters the lumen of the vessel beyond the occlusion.

In a further aspect, an external imaging system, such as a flurosystem, may be used to image the treating catheter in an image plane that is generally perpendicular to the imaging plane of the imaging system 268. In one aspect, the display 400 includes both an image 300 from the imaging system and an image from the flurosystem. In another aspect, a multi-dimensional model is generated based on inputs from the imaging system 268 and another imaging system and the resulting data is displayed to a user. In this form, the resulting data provided on display 400 may include colorized portions indicating vessel structures, tissues, and the crossing wire. In this form, both the output of the imaging system 268 and the output of the flurosystem may be used to position the treating device, identify a path for crossing the occlusion and monitor progression of the crossing wire as it extends from the delivery catheter.

Although the above method of use has been described in relation to crossing a vessel occlusion, it will be appreciated that the system can used to treat structural tissue defects as well. In one example, the treating system may be guided to a patient's heart. The imaging system 268 is used to image tissue within the heart, such as a valve or a wall, to identify a defect. Once the defect is identified, the treating device is rotated about the longitudinal axis to align the visual indicator with the identified defect. If necessary, the longitudinal position of the opening in the catheter where the treating device exits can be adjusted so the treating device is properly aligned with the tissue to be treated. The treating device can then be steered by the control system to exit the catheter and extend in a direction toward the tissue to be treated. For a heart valve or structural wall defect, the treating system may include a tacking or tissue joining device, such as a T-bar, for joining one tissue structure to another. Alternatively, the treating system may include an ablation device to damage tissue. The imaging system may be utilized to monitor the therapy being delivered in real time. During treatment monitoring, the location of the treatment device may be adjusted by the steering assembly based on image data displayed to the user.

While the invention has been described in connection with specific embodiments thereof, it is to be understood that this is by way of illustration and not of limitation, and the scope of the appended claims should be construed as broadly as the prior art will permit.

What is claimed is:

1. A method of crossing an occlusion within a vessel, the method comprising:
positioning a catheter within a vessel of a patient, the catheter including:
an imaging element,
a steering assembly comprising a first tube and a second tube, wherein the first tube is located within the second tube and slides with respect to the second tube, wherein the first and second tubes are telescopically movable with respect to each other, an occlusion crossing wire extending out of an opening in the first tube through a side port in the second tube that provides an exit opening in a side of the catheter, a stabilizing element that provides stability to the catheter located either proximal to or distal to the exit opening, and a visual marker element positioned on the catheter and aligned with the exit opening in the catheter, the visual marker element configured to be within a field of view captured by the imaging element;

advancing the imaging element through a main vessel to a position adjacent an occlusion of a side vessel;

imaging the occlusion along with a portion of the side vessel;

aligning the exit opening in the side of the catheter with the occlusion based on a visual indication of an orientation of the exit opening with respect to the imaged occlusion and the side vessel provided by the visual marker element;

changing an orientation of the crossing wire with the steering assembly by moving the second tube telescopically with respect to the first tube, thereby to cause the crossing wire to change its angle with respect to the catheter; and advancing the crossing wire through the opening of the first tube and the exit opening in the side of the catheter and into the occlusion.

2. The method of claim 1, wherein the imaging includes evaluating tissue characteristics of at least one of the occlusion and the side vessel.

3. The method of claim 1, wherein the catheter includes the marker detectible by the imaging element, and the aligning further includes rotationally aligning the marker with the side vessel.

4. The method of claim 1, wherein the imaging includes activating at least one ultrasound transducer.

5. The method of claim 1, wherein the imaging includes activating an optical coherence tomography sensing system.

6. The method of claim 1, wherein the steering assembly includes an inner catheter positioned within the catheter, the crossing wire extending within at least a portion of the inner catheter and exiting a distal opening; and further including moving the inner catheter with respect to the exit opening to thereby change the alignment of the crossing wire before advancing the crossing wire through the exit opening.

7. The method of claim 1, further including imaging the side branch vessel and the crossing wire during the advancing the crossing wire through the exit opening and into the occlusion.

8. The method of claim 7, further including adjusting the path of the crossing wire utilizing the steering assembly based on the imaging during the advancing of the crossing wire.

9. A vessel occlusion crossing system comprising:

a catheter body having a lumen and a side port that provides an exit opening in a side of the catheter body;

an imaging element disposed on a distal portion of the catheter;

a crossing wire;

a steering assembly comprising a first tube slidably located within the lumen of the catheter body, wherein the first tube is telescopically movable within the lumen of the catheter body, wherein the crossing wire is slidably disposed within the first tube, and wherein the crossing wires are configured to extend to the side port in the side of the catheter body, the steering assembly configured to change a direction of the crossing wire after exit through the side port by moving the first tube telescopically with respect to the lumen of the catheter body thereby to cause the crossing wire to change its angle with respect to the catheter body;

a stabilizing element that provides stability to the catheter located either proximal to or distal to the exit opening; and a visual marker element positioned on the catheter and aligned with the exit opening in the catheter, the visual marker element configured to be within a field of view captured by the imaging element and further configured to provide a visual indication of the orientation of the exit opening of the catheter with respect to an imaged vessel occlusion.

10. The system of claim 9, wherein the imaging element includes an ultrasound transducer.

11. The system of claim 9, wherein the imaging element comprising an array of ultrasound transducers.

12. The system of claim 10, wherein the ultrasound transducer is rearward looking away from a distal end of the catheter body.

13. The system of claim 9, further including a communication connector coupled to the imaging element, the communication connector extending within at least a portion of the catheter.

14. The system of claim 13, the communication connector is embedded into a sidewall of the catheter.

15. The system of claim 9, further including a balloon carried by the catheter.

* * * * *